United States Patent
Sugano et al.

(10) Patent No.: US 11,341,999 B2
(45) Date of Patent: May 24, 2022

(54) MEDICAL VIDEO PROCESSING SYSTEM

(71) Applicant: Medi Plus Inc., Tokyo (JP)

(72) Inventors: Naoya Sugano, Tokyo (JP); Minsu Kwon, Tokyo (JP)

(73) Assignee: MEDI PLUS INC., Tokyo (JP)

( * ) Notice: Subject to any disclaimer, the term of this patent is extended or adjusted under 35 U.S.C. 154(b) by 0 days.

(21) Appl. No.: 16/956,874

(22) PCT Filed: Nov. 1, 2018

(86) PCT No.: PCT/JP2018/040759
§ 371 (c)(1),
(2) Date: Jun. 22, 2020

(87) PCT Pub. No.: WO2019/130813
PCT Pub. Date: Jul. 4, 2019

(65) Prior Publication Data
US 2021/0065746 A1    Mar. 4, 2021

(30) Foreign Application Priority Data

Dec. 27, 2017    (JP) .............................. JP2017-251482

(51) Int. Cl.
*G11B 27/031*    (2006.01)
*A61B 90/00*    (2016.01)
(Continued)

(52) U.S. Cl.
CPC .......... *G11B 27/031* (2013.01); *A61B 90/361* (2016.02); *G11B 27/002* (2013.01);
(Continued)

(58) Field of Classification Search
CPC ..... G11B 27/031; G11B 27/002; G11B 27/34; G11B 27/102; A61B 90/361;
(Continued)

(56) References Cited

U.S. PATENT DOCUMENTS 10,223,591 B1 *    3/2019    Goldenberg ............. H04N 5/91
10,440,346 B2 *    10/2019    Sugano ................. G06F 3/1454
(Continued)

FOREIGN PATENT DOCUMENTS

CN    1589570 A    3/2005
CN    101379824 A    3/2009
(Continued)

OTHER PUBLICATIONS

International Search Report dated Dec. 11, 2018, issued in counterpart International Application No. PCT/JP2018/040759 (2 pages).
(Continued)

*Primary Examiner* — Thai Q Tran
*Assistant Examiner* — Stephen R Smith
(74) *Attorney, Agent, or Firm* — Westerman, Hattori, Daniels & Adrian, LLP

(57) ABSTRACT

The medical video processing system is provided with: an encoder 120 that inputs a plurality of video files about a surgical operation, separating the plurality of video files according to a plurality of input systems; a server apparatus 130; and a viewing terminal apparatus 140. The viewing terminal apparatus 140 displays a plurality of timelines related to the plurality of video files, separating the plurality of timelines according to input systems; and synchronously displays, among images included in the plurality of video files corresponding to the displayed timelines, at least a part of a plurality of images associated with a time code of a certain time point included in the time lines, and accepts an operation input by a user to execute editing processing about video files synchronously displayed in a synchronous display area.

7 Claims, 15 Drawing Sheets

(51) Int. Cl.
- *G11B 27/00* (2006.01)
- *G11B 27/10* (2006.01)
- *G11B 27/34* (2006.01)
- *H04N 5/232* (2006.01)
- *H04N 5/247* (2006.01)
- *H04N 5/77* (2006.01)
- *H04N 7/18* (2006.01)

(52) U.S. Cl.
CPC ............ *G11B 27/102* (2013.01); *G11B 27/34* (2013.01); *H04N 5/23216* (2013.01); *H04N 5/247* (2013.01); *H04N 5/77* (2013.01); *H04N 7/18* (2013.01); *A61B 2090/371* (2016.02)

(58) Field of Classification Search
CPC .............. A61B 2090/371; H04N 5/77; H04N 5/23216; H04N 5/247; H04N 7/18
USPC .............. 386/223, 278; 705/2; 382/705, 128
See application file for complete search history.

(56) References Cited

U.S. PATENT DOCUMENTS

| | | |
|---|---|---|
| 2005/0066047 A1 | 3/2005 | Miyake et al. |
| 2008/0306766 A1* | 12/2008 | Ozeki .................... G06Q 10/06 705/2 |
| 2009/0022474 A1 | 1/2009 | Kubono et al. |
| 2015/0008220 A1 | 1/2015 | Wang |
| 2015/0016700 A1 | 1/2015 | Drozdzal et al. |
| 2015/0302605 A1* | 10/2015 | Sasaki .................... A61B 6/486 382/128 |
| 2017/0099479 A1* | 4/2017 | Browd .................... A61B 34/20 |
| 2017/0364600 A1* | 12/2017 | Sadauskas, Jr. ....... G06F 16/248 |
| 2018/0122506 A1* | 5/2018 | Grantcharov .......... G16H 50/50 |
| 2018/0131844 A1* | 5/2018 | Lau ........................ H04N 7/188 |
| 2019/0012332 A1* | 1/2019 | Newman ............... H04N 1/2158 |
| 2019/0019533 A1* | 1/2019 | Kaufman .......... H04N 21/47205 |
| 2020/0066305 A1* | 2/2020 | Spence ............. H04N 21/8549 |
| 2020/0268471 A1* | 8/2020 | Kajita ................ H04N 5/23293 |

FOREIGN PATENT DOCUMENTS

| | | |
|---|---|---|
| EP | 3018578 A1 | 5/2016 |
| JP | 2001-195869 A | 7/2001 |
| JP | 2002-272758 A | 9/2002 |
| JP | 2008-301984 A | 12/2008 |
| JP | 2015-509026 A | 3/2015 |
| JP | 2015-211831 A | 11/2015 |
| JP | 2016-530051 A | 9/2016 |
| WO | 2016/046906 A1 | 3/2016 |
| WO | WO-2016046906 A1 * | 3/2016 ........... H04N 21/475 |

OTHER PUBLICATIONS

Office Action dated Sep. 24, 2021, issued in counterpart CN Application No. 201880084167.7, with English Translation. (27 pages).

* cited by examiner

MEDICAL VIDEO PROCESSING SYSTEM

TECHNICAL FIELD

The present invention relates to a medical video processing system.

BACKGROUND ART

Recently, for the purpose of securing a plurality of viewpoints in a surgery or recording content of the surgical operation, a medical video processing system not only for directly visually confirming an affected part but also for shooting video using a plurality of shooting apparatuses and displaying the video on a monitor has existed.

As conventional inventions about this kind of medical video processing system, Patent documents 1 and 2 below are shown.

Patent document 1 discloses an invention in which control information about a remotely operated surgical tool, image information obtained by shooting an affected part and the surgical tool, biological information about a patient and the like are recorded, together with a unified time code, and a surgical operation is reproduced based on the recorded time code and the pieces of information.

Patent document 2 discloses an invention in which editing processing for attaching commands (pointers and a user's comments) to medical video is performed, and, at the time of reproducing the edited video, a given command is displayed at specified time.

CITATION LIST

Patent Documents

Patent document 1: Japanese Patent Laid-Open No. 2002-272758
Patent document 2: Japanese Patent Laid-Open No. 2001-195869

SUMMARY OF THE INVENTION

Problem to be Solved by the Invention

In the invention according to Patent document 1, although it is possible to cut out a part of a surgical operation at specified time, based on a time code, it is not possible to cut out the part while checking content of the surgical operation at the specified time, and, therefore, work for checking video after the surgical operation requires much time.

In the invention according to Patent document 2, although it is possible to, by attaching commands to medical video, support checking of the video after a surgical operation, the editing is such that is performed for medical video displayed on a main screen (a central part of a monitor in FIG. 13 of Patent document 2), and there is a lack of an idea for video displayed on sub-screens (an upper left corner part of the monitor in FIG. 13 of Patent document 2).

The present invention has been made in view of the above problems and provides a medical video processing system that facilitates editing work about a medical video file.

Means for Solving the Problem

According to the present invention, there is provided a medical video processing system including: a video input unit that inputs a plurality of video files about a surgical operation, separating the plurality of video files according to a plurality of input systems; a storage unit that stores the plurality of video files inputted by the video input unit in association with a common time code specified with a certain time point in a period during which the surgical operation is performed as a start point; a display unit that displays the plurality of video files stored in the storage unit and information about the video files; and an operation input unit that accepts an operation input by a user to the display unit; wherein a display area of the display unit includes: a timeline display area to display a plurality of timelines indicating time zones corresponding to the plurality of video files about the surgical operation, separating the plurality of timelines according to the input systems; and a synchronous display area to synchronously display, among images included in the plurality of video files corresponding to the timelines displayed in the timeline display area, at least a part of a plurality of images associated with the time code of the certain time point included in the time lines; and the medical video processing system further includes an editing unit that executes editing processing about the video files synchronously displayed in the synchronous display area, based on an operation input accepted by the operation input unit.

According to the above invention, video files about a surgical operation are synchronously displayed, and a user can perform editing processing for each video file while checking content of the video file and a timeline and, therefore, can easily perform editing work of the video file.

Effect of the Invention

According to the present invention, there is provided a medical video processing system that facilitates editing work about a medical video file.

DESCRIPTION OF EMBODIMENT

Figure 1:
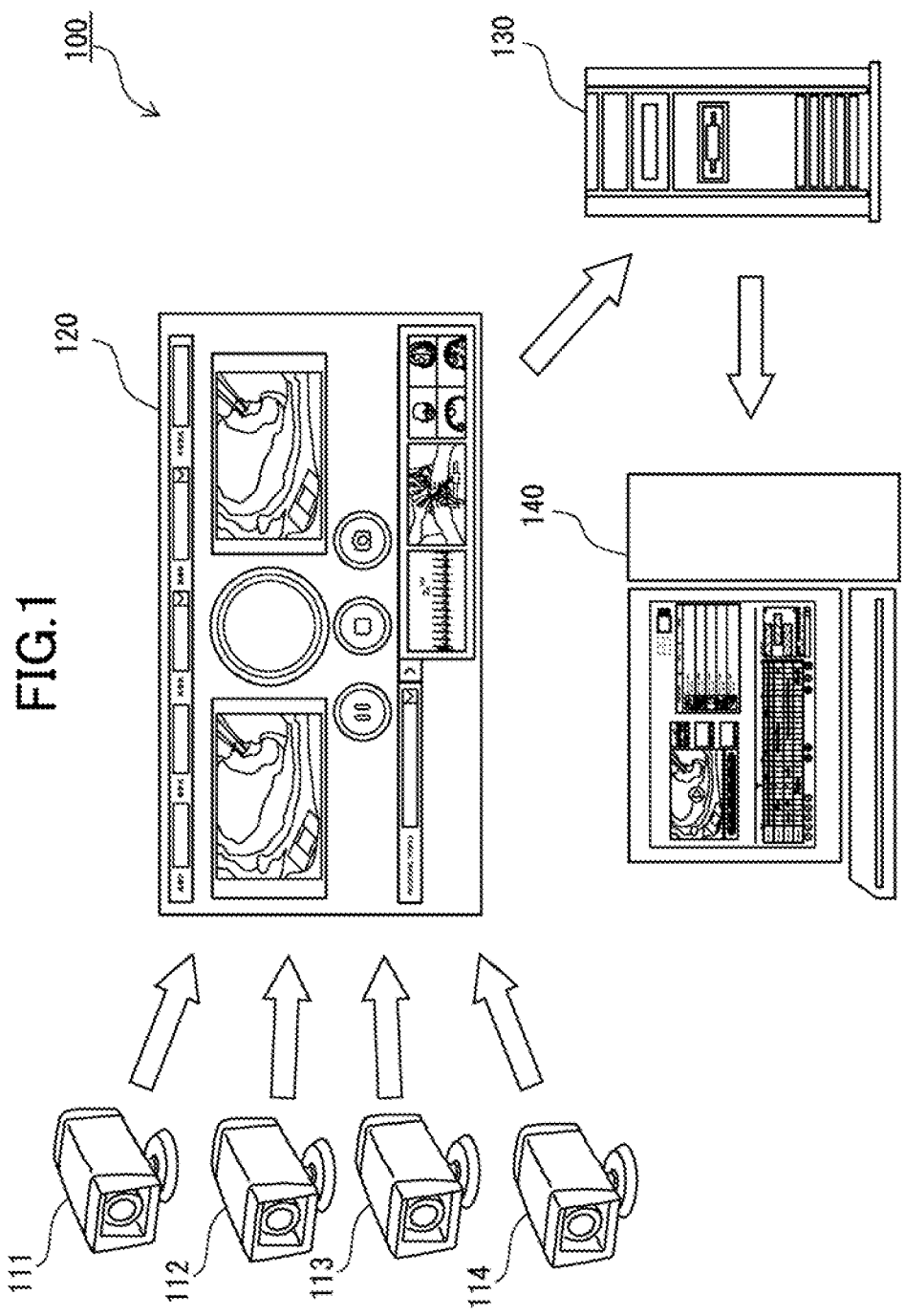
FIG. 1 is a diagram showing a medical video processing system according to the present embodiment.

An embodiment of the present invention will be described below with reference to the drawings. Note that, in all the drawings, similar components are given the same reference numerals, and description thereof will not be repeated.
<Components Included in Medical Video Processing System 100>

FIG. 1 is a diagram showing a medical video processing system (hereinafter referred to as a medical video processing system 100) according to the present embodiment.

Arrows shown in FIG. 1 indicate output sources and input destinations of video files given and received among components. Therefore, as for giving and receiving of information and data other than video files, the giving and receiving do not necessarily have to correspond to content indicated by each arrow.

In description below, a video file may be a file configured only with video data or may be what includes video data and voice data.

The medical video processing system 100 is provided with a plurality of shooting apparatuses (cameras 111 to 114), an encoder 120, a server apparatus 130 and a viewing terminal apparatus 140.

The cameras 111 to 114 are shooting apparatuses that shoot a surgically operated person (a patient) who is undergoing a surgical operation and surroundings around the surgically operated person to generate a video file.

For example, the cameras 111 and 113 are cameras to shoot a surgical field of the surgical operation, and the camera 113 shoots a wider range in comparison with the camera 111. The camera 112 shoots a heart rate monitor, and the camera 114 shoots a monitor that displays a magnetic resonance imaging (MRI) image or the like. The cameras 112 and 114 shares a role of shooting a biological information monitor that displays biological information about the surgically operated person of the surgical operation.

Note that the number and shooting targets of the cameras 111 to 114 mentioned here are mere examples and do not restrict the embodiment of the present invention.

The encoder 120 performs encode processing (encoding) for video files generated by the cameras 111 to 114 to convert the video files to a format suitable for transfer to and storage into the server apparatus 130.

Note that it is preferable that the encoder 120 performs compression processing for the video files to cause the video files to be stored into the server apparatus 130. This is because the size of the video files stored into the server apparatus 130 can be reduced thereby.

The encoder 120 performs control about shooting by the cameras 111 to 114 based on a user operation, and separates video files about a surgical operation generated by the shooting according to a plurality of input systems (according to the cameras 111 to 114) to input the video files. In other words, the encoder 120 constitutes a video input unit and a shooting control unit according to the present invention.

Here, the "control about shooting by the cameras 111 to 114" refers to causing the cameras 111 to 114 to execute start of recording, pause of recording and stop of recording of video, and shooting of a still image in the present embodiment. Note that the content of the control about shooting by the cameras 111 to 114 mentioned here is mere examples and does not restrict the embodiment of the present invention.

The server apparatus 130 stores the video files transferred from the encoder 120. More specifically, the server apparatus 130 stores the plurality of video files inputted by the encoder 120 in association with a common time code specified with a certain time point in a period in which the surgical operation is performed, as a start point. In other words, the server apparatus 130 constitutes a storage unit according to the present invention.

Here, the time code is time-series information (information about order of frames constituting a video file) associated with video file, and it is preferable that the time code is given for each frame. The start point of the time code may be freely specified by a user of the encoder 120 (for example, a surgical operator or his/her assistant) within the period in which the surgical operation is performed, or a signal indicating the start time point of the surgical operation may be inputted from an external apparatus (not shown in the drawings) to specify the signal as a trigger.

The viewing terminal apparatus 140 is a computer apparatus in which application software (a viewer) for reproducing the video files stored in the server apparatus 130 is installed.

The viewing terminal apparatus 140 accesses the video files stored in the server apparatus 130 to display (synchronously reproduce) the plurality of video files associated with the common time code. Furthermore, the viewing terminal apparatus 140 can also display information about the video files that are being synchronously reproduced together. Further, the viewing terminal apparatus 140 can accept a user operation input thereto and execute editing processing about the video files displayed in a synchronous display area to be described later, based on the accepted operation input. In other words, the viewing terminal apparatus 140 constitutes a display unit and an operation input unit according to the present invention.

In description below, "display of a video file" and "reproduction of a video file" are almost synonymous and are used without distinction.

Although it is shown in FIG. 1 as if there were a single viewing terminal apparatus 140, the medical video processing system 100 may be provided with a plurality of viewing terminal apparatuses 140. The viewer installed in the viewing terminal apparatus 140 does not necessarily have to be realized by application software dedicated to the present invention but may be realized by general-purpose application software (for example, an internet browser) or software obtained by improving or changing the general-purpose application software.

The server apparatus 130 can execute the editing processing about the video files synchronously displayed in a part (the synchronous display area to be described later) of a display area of the viewing terminal apparatus 140 based on an operation input accepted by the viewing terminal apparatus 140. In other words, the server apparatus 130 constitutes an editing unit according to the present invention.

In the present embodiment, the server apparatus 130 (the editing unit) and the viewing terminal apparatus 140 (the display unit and the operation input unit) are realized as individual apparatuses. The reason is as follows. In order to enable the editing processing to be executed in the viewing terminal apparatus 140, it is necessary to execute the editing processing after transferring an editing target video file from the server apparatus 130 to the viewing terminal apparatus 140. If such a system configuration is adopted, it becomes difficult to ensure adequate security for management of the video files in the medical video processing system 100 (the server apparatus 130), and there is a possibility that inappropriate leakage of a video file is invited.

Medical video files are highly confidential personal information, and the medical video processing system 100 of the present embodiment adopts the configuration described above in order to prevent leakage of the video files outside.

<Operation of the Encoder 120>

Next, operation of the encoder 120 will be described with reference to FIGS. 2 to 4.

Figure 2:
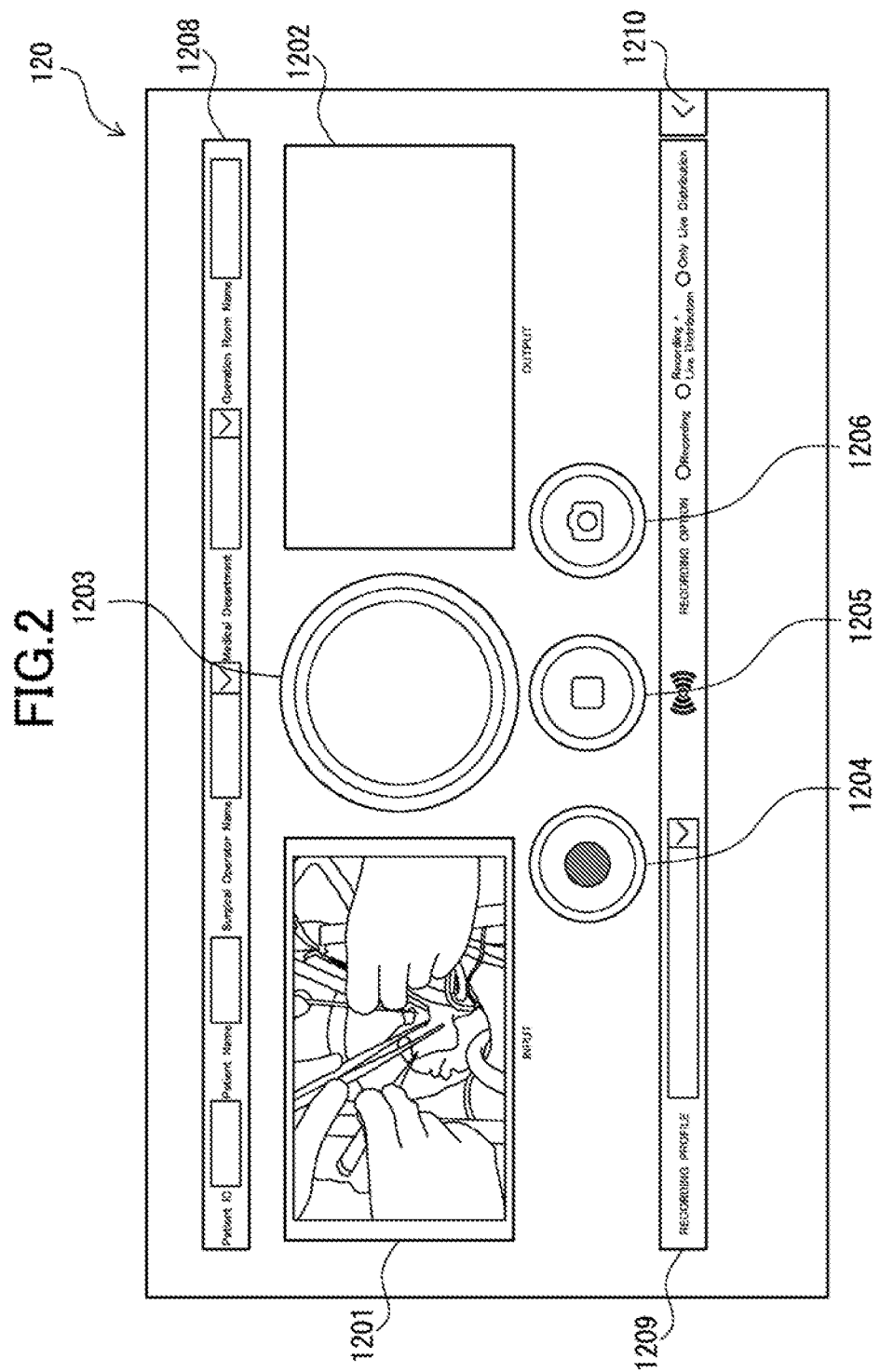
FIG. 2 is a diagram showing a specific example of a screen displayed in a display area of an encoder.
Figure 3:
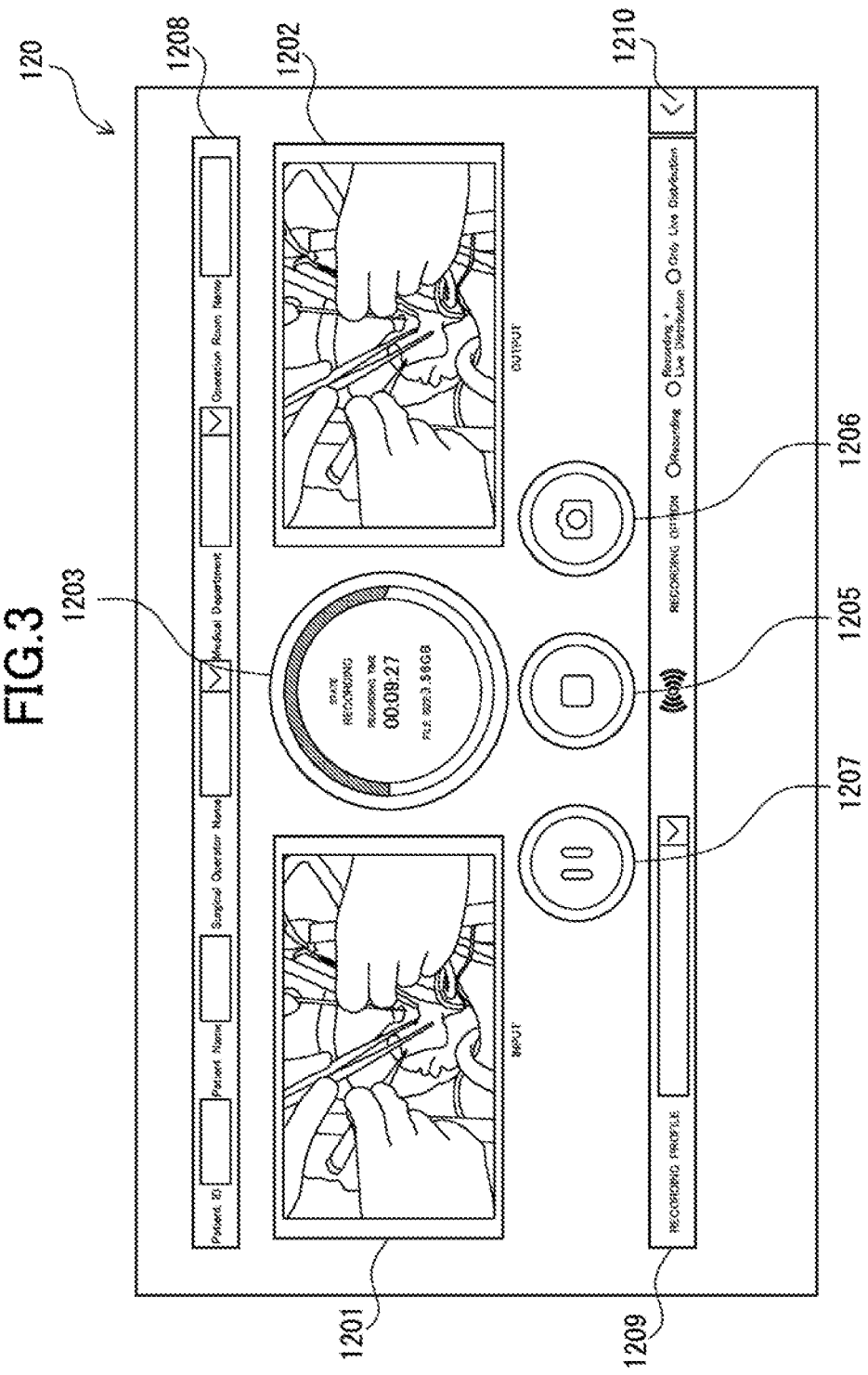
FIG. 3 is a diagram showing a specific example of the screen displayed in the display area of the encoder.
Figure 4:
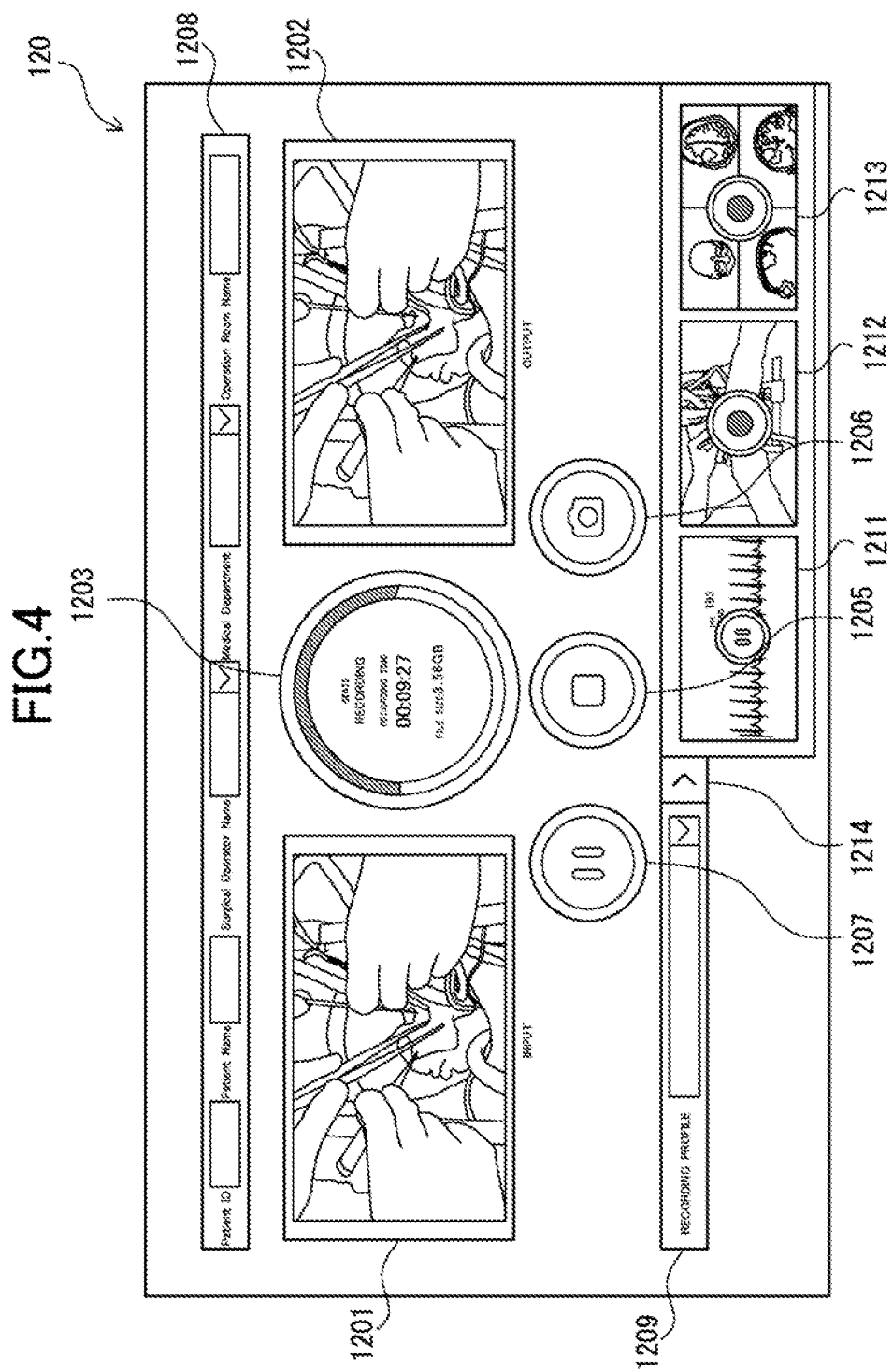
FIG. 4 is a diagram showing a specific example of the screen displayed in the display area of the encoder.

FIGS. 2 to 4 are diagrams showing specific examples of a screen displayed in a display area of the encoder 120. FIG. 2 is a diagram showing the display area of the encoder 120 before recording. FIG. 3 is a diagram showing the display area of the encoder 120 during recording. FIG. 4 is a diagram showing the display area of the encoder 120 in a case where an enlarged screen is displayed during recording.

The display area of the encoder 120 functions as a graphical user interface (GUI), and the user can operate the encoder 120 by operating an icon or the like on a display using an input device (a mouse, a keyboard or the like) not shown in the drawings, which is attached to the encoder 120. When the display area of the encoder 120 is a touch panel, the display area itself functions as an input device.

In the display area of the encoder 120, an input screen 1201, an output screen 1202 and a state display 1203 are displayed.

The input screen 1201 is a screen to reproduce any of video files inputted from the cameras 111 to 114. For example, FIGS. 2 to 4 show a state in which a video file inputted from the camera 111 is being reproduced on the input screen 1201.

The output screen 1202 is a screen to reproduce a video file outputted from the encoder 120 to the server apparatus 130. Output formats by the encoder 120 include a recording format (an output format to cause an inputted video file to be stored into the server apparatus 130), a live format (an output format to output an inputted video file to the viewing terminal apparatus 140 in a manner that the video file can be live-distributed) and a combination of the recording format and the live format. The display area of the encoder 120 shown in FIGS. 3 and 4 is the display area in a case where the encoder 120 is outputting video files in the recording format.

The state display 1203 shows a state of a video file being reproduced on the output screen 1202 at that time point, that is, a video file being outputted to the server apparatus 130. Specifically, in the state display 1203, which output format a video file is being outputted in, a time during which output is being performed, a data size of the outputted video file, and the like are displayed.

In the display area of the encoder 120, a recording start button 1204, a recording stop button 1205, a still image shooting button 1206 and a recording pause button 1207 are displayed.

The recording start button 1204 is a button to accept an operation to be a trigger for staring recording of a video file being reproduced on the input screen 1201 (processing for storage into the server apparatus 130).

The recording stop button 1205 is a button to accept an operation to be a trigger for stopping recording of a video file (processing for storage into the server apparatus 130).

The still image shooting button 1206 is a button to accept an operation to be a trigger for causing one frame of a video file being reproduced on the input screen 1201 to be stored into the server apparatus 130 as a still image.

The recording pause button 1207 is a button to accept an operation to be a trigger for pausing recording of a video file (processing for storage into the server apparatus 130) or an operation to be a trigger for releasing pause.

Note that the recording start button 1204 is not displayed during a period during which a video file is being recorded (including a period during which recording is paused), and the recording pause button 1207 is not displayed during a period during which a video file is not being recorded. Therefore, if the recording start button 1204 is operated during the period during which recording is not being operated, the recording start button 1204 is replaced with the recording pause button 1207; and, if the recording stop button 1205 is performed during the period during which recording is being performed, the recording pause button 1207 is replaced with the recording start button 1204.

In the display area of the encoder 120, a surgical operation information display 1208 and an output information display 1209 are displayed.

The surgical operation information display 1208 displays information related to a surgical operation of a video file being reproduced on the input screen 1201, specifically, an identification number and name of a surgically operated person (a patient), a name of a surgical operator, a name of a medical department, a name of a place where the surgical operation is being performed, and the like. The name of a surgical operator and the name of a medical department can be selected by a user operation input to the surgical operation information display 1208. As for information that does not require a user operation input, among the pieces of information displayed on the surgical operation information display 1208, the information may be imported from an external system (for example, an electronic medical record system or the like) not shown in the drawings.

The output information display 1209 displays a file format of a video file being reproduced on the output screen 1202, whether or not voice output is being performed together with reproduction of the video file, and in which output format output to the server apparatus 130 is performed. The pieces of information displayed on the output information display 1209, which have been given here, can be selected by a user operation input to the output information display 1209.

In the display area of the encoder 120, an extended display activation button 1210 and an extended display stop button 1214 are displayed.

The extended display activation button 1210 is a button to accept an operation to be a trigger for turning on an extended display area where a video file inputted from an input system different from an input system of a video file being reproduced on the input screen 1201 or the output screen 1202 is to be reproduced. For example, FIG. 4 shows a state in which, in the extended display area, a video file inputted from the camera 112, a video file inputted from the camera 113 and a video file inputted from the camera 114 are displayed on a sub-screen 1211, a sub-screen 1212 and a sub-screen 1213, respectively. When a video file reproduced in the extended display area is being recorded in the above state, an icon similar to the recording pause button 1207 is displayed being superimposed on the video file. By operating this icon, recording is paused. Further, when a video file reproduced in the extended display area is not being recorded in the above state, an icon similar to the recording start button 1204 is displayed being superimposed on the video file. By operating this icon, recording is started.

The extended display stop button 1214 is a button which is displayed when the above extended display area is displayed and accepts an operation to be a trigger for turning off the extended display area.

<Synchronous Display on Viewing Terminal Apparatus 140>

Next, a synchronous display on the viewing terminal apparatus 140 will be described with reference to FIGS. 5 to 12.

Figure 5:
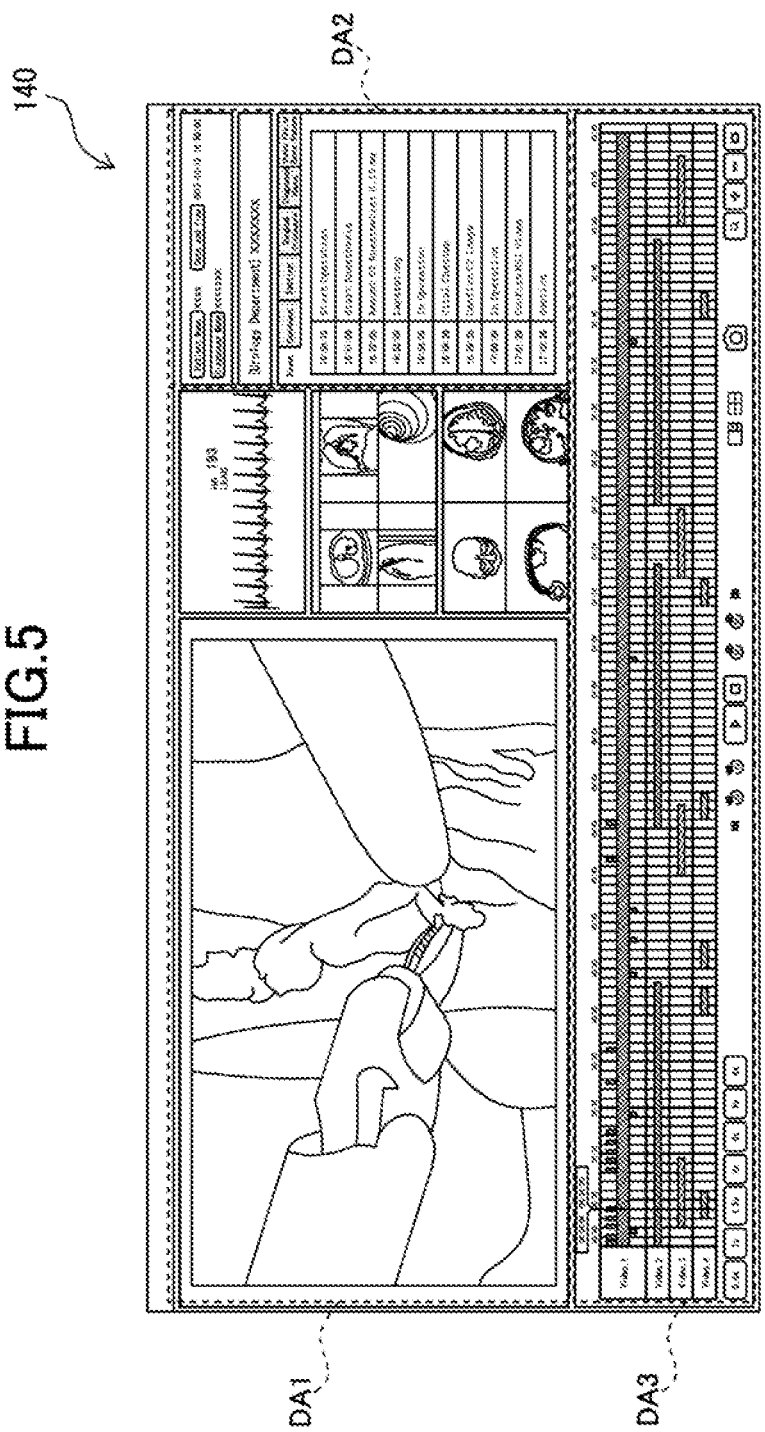
FIG. 5 is a diagram showing a specific example of a screen displayed in a display area of a viewing terminal apparatus.
Figure 6:
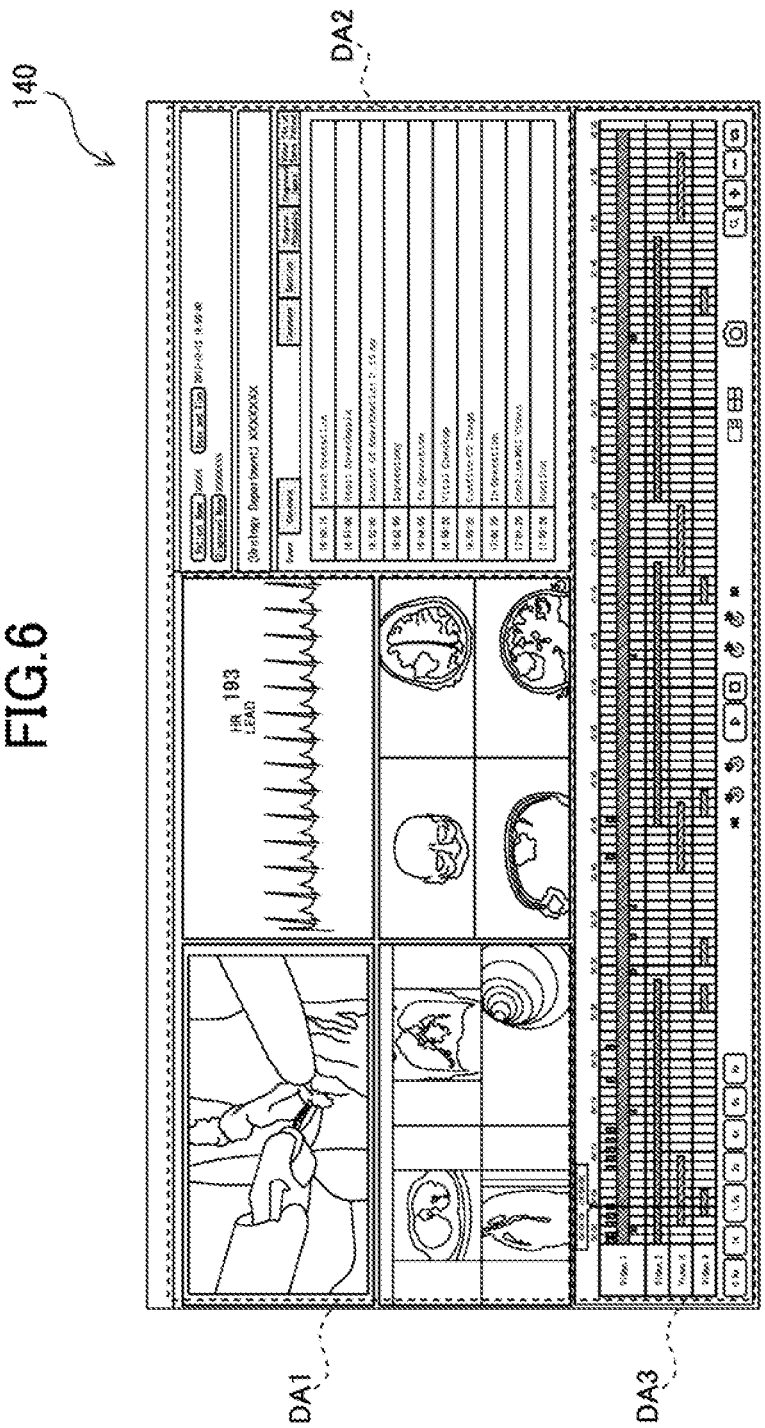
FIG. 6 is a diagram showing a specific example of the screen displayed in the display area of the viewing terminal apparatus.
Figure 7:
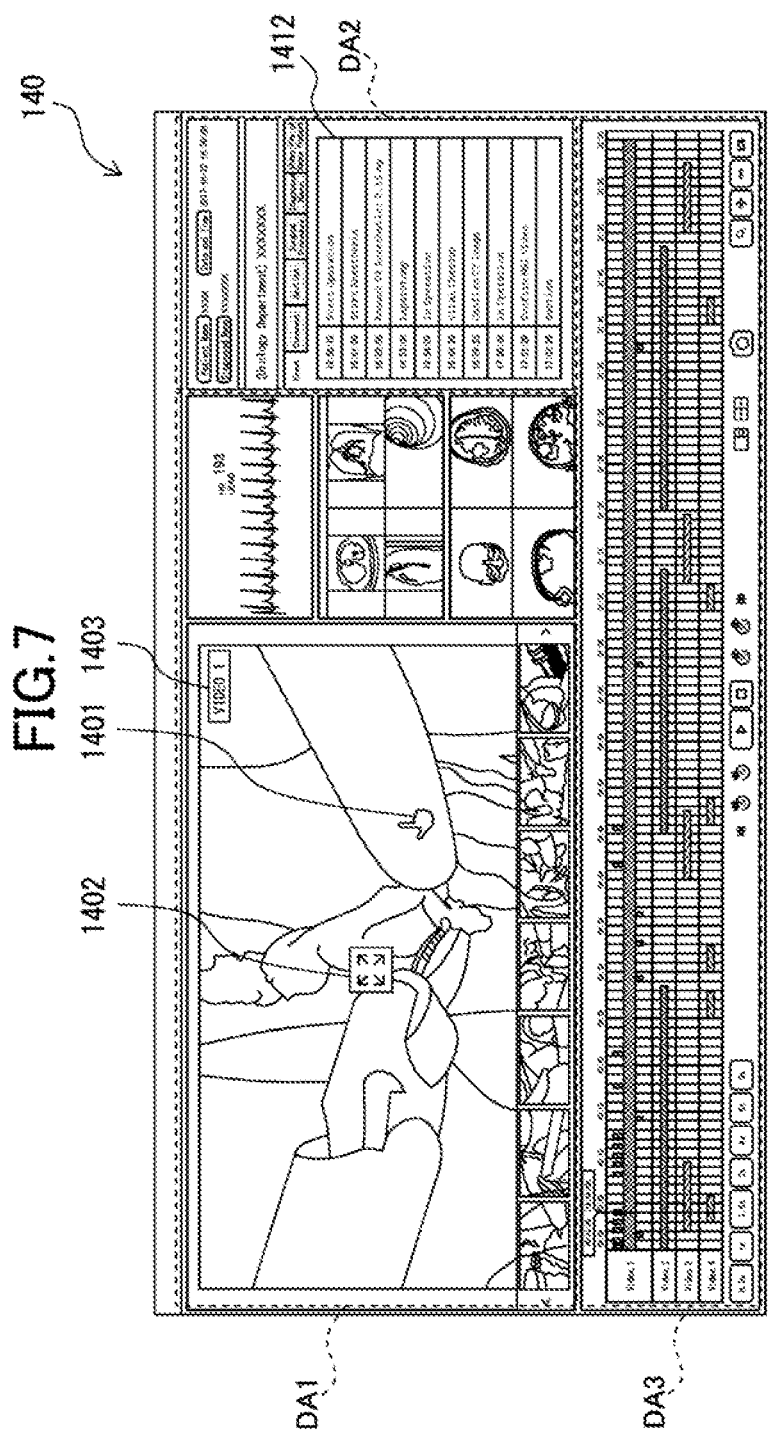
FIG. 7 is a diagram showing a specific example of the screen displayed in the display area of the viewing terminal apparatus.
Figure 8:
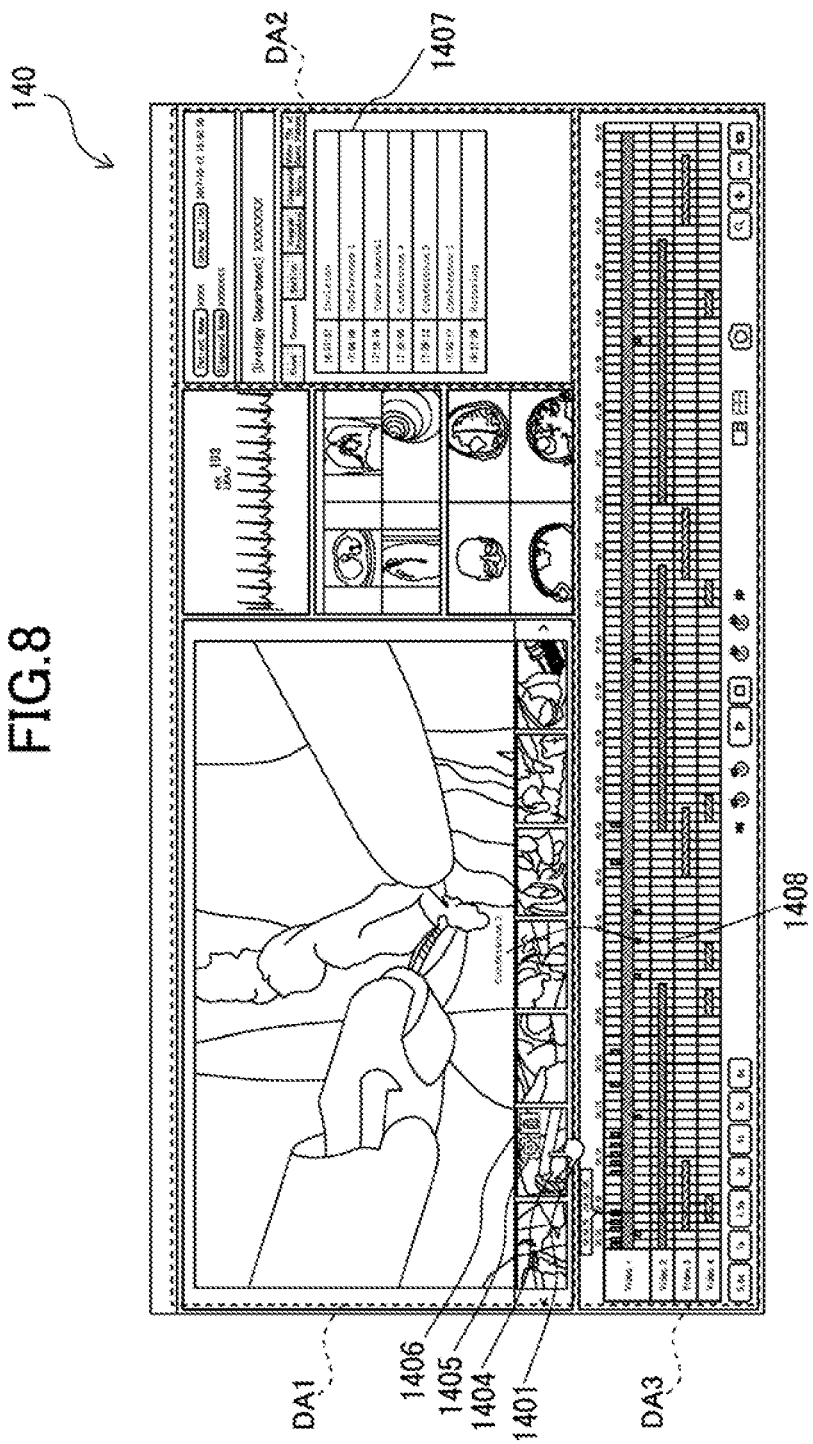
FIG. 8 is a diagram showing a specific example of the screen displayed in the display area of the viewing terminal apparatus.
Figure 9:
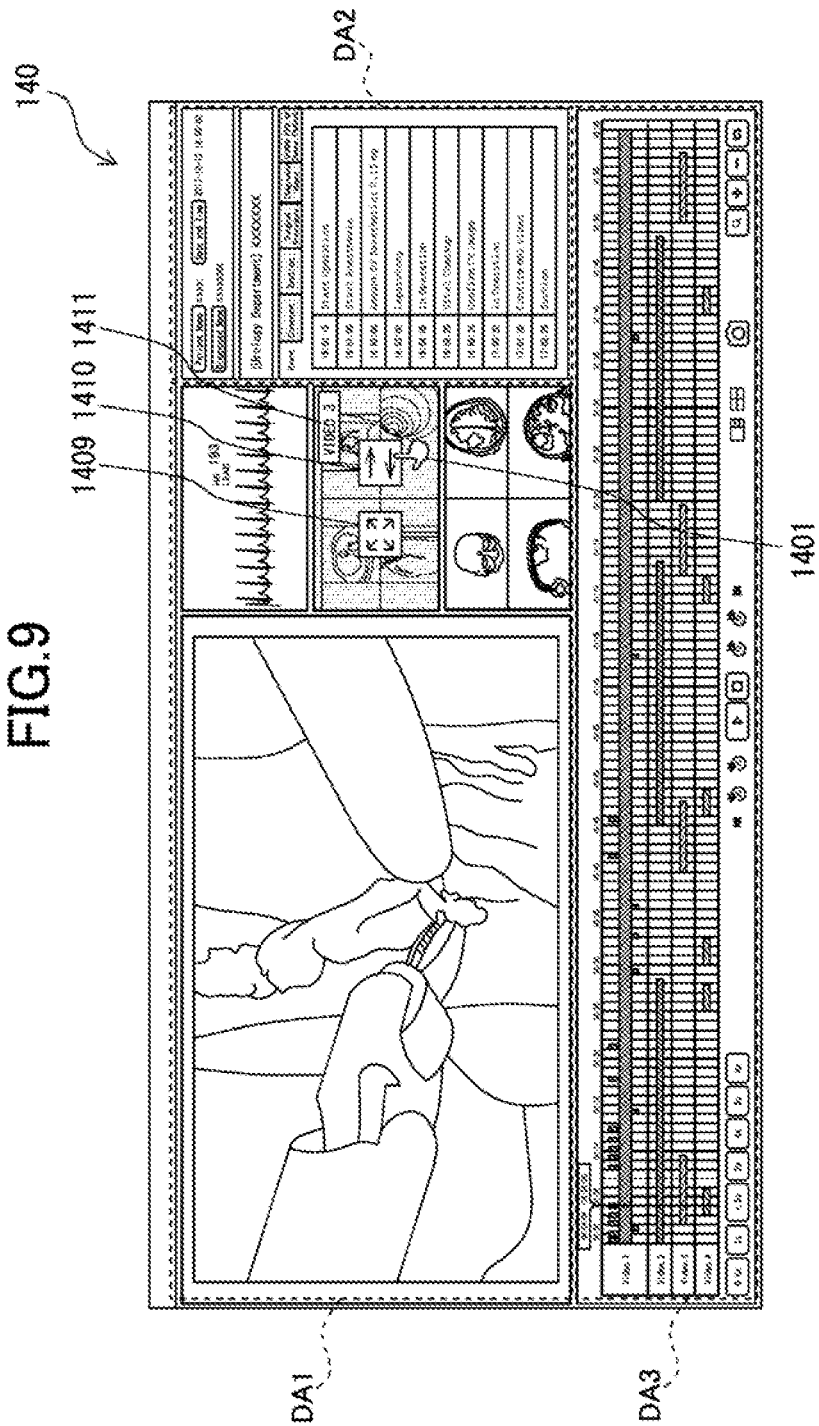
FIG. 9 is a diagram showing a specific example of the screen displayed in the display area of the viewing terminal apparatus.

FIGS. 5 to 9 are diagrams showing specific examples of a screen displayed in the display area of the viewing terminal apparatus 140. More specifically, FIG. 5 is a diagram showing a display aspect in which, in a synchronous display area DA1, one video file is reproduced on a main screen, and other video files are reproduced on sub-screens. FIG. 6 is a diagram showing a display aspect in which the synchronous display area DA1 is divided in four, and four video files are reproduced in the four, respectively. FIG. 7 is a diagram showing a state in which a cursor is positioned on the main screen in the synchronous display area DA1. FIG. 3 is a diagram showing a state in which the cursor is positioned on a still image displayed below the main screen in the synchronous display area DA1. FIG. 9 is a diagram showing a state in which the cursor is positioned on a sub-screen in the synchronous display area DA1.

Figure 10:
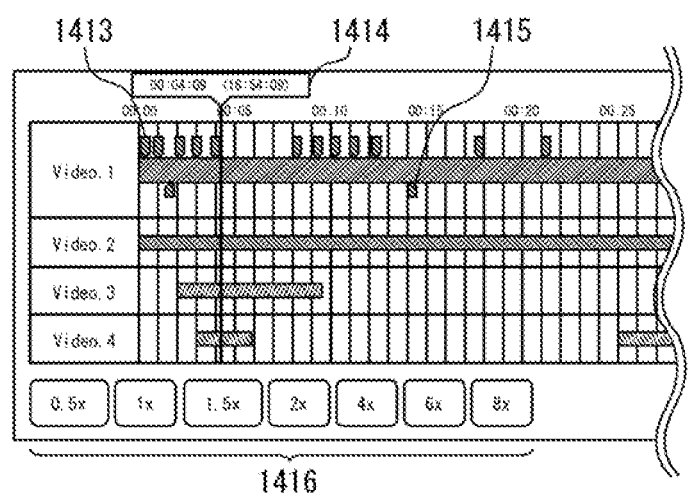
FIG. 10 is an enlarged view in which a part of a timeline display area is enlarged.
Figure 11:
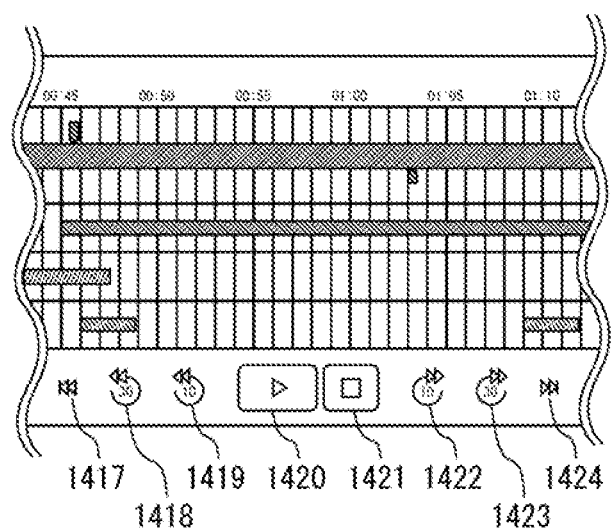
FIG. 11 is an enlarged view in which a part of the timeline display area is enlarged.
Figure 12:
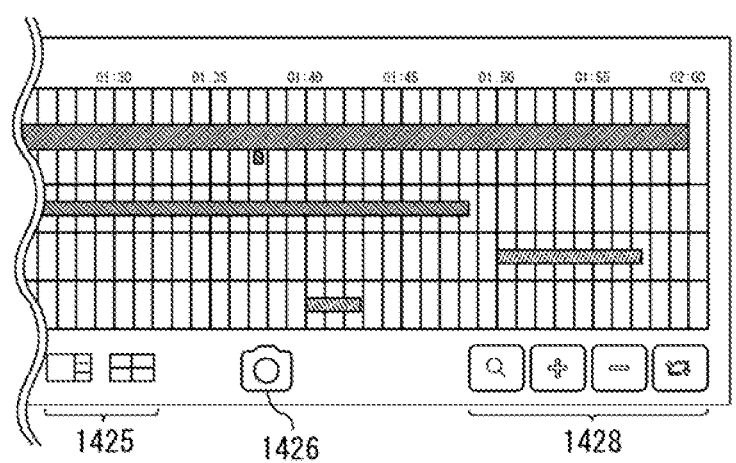
FIG. 12 is an enlarged view in which a part of the timeline display area is enlarged.

FIGS. 10 to 12 are enlarged views in which a part of a timeline display area DA3 is enlarged. More specifically, FIG. 10 is an enlarged view in which a left part of the timeline display area DA3 is enlarged. FIG. 11 is an enlarged view in which a central part, of the timeline display area DA3 is enlarged. FIG. 12 is an enlarged view in which a right part of the timeline display area DA3 is enlarged.

The display area of the viewing terminal apparatus 140 functions as a graphical user interface, and the user can operate the viewing terminal apparatus 140 by operating an icon or the like on a display using an input device not shown in the drawings, which is attached to the viewing terminal apparatus 140. When the display area of the viewing terminal apparatus 140 is a touch panel, the display area itself functions as an input device.

In description below, the cursor pointing a target of an operation by the input device will be referred to as a pointer 1401.

The display area of the viewing terminal apparatus 140 includes the synchronous display area DA1, a related information display area DA2 and the timeline display area DA3.

Note that ranges indicated by broken lines in FIGS. 5 to 9 show ranges of the display areas enumerated here and are not ranges actually displayed on the display area of the viewing terminal apparatus 140.

The synchronous display area DA1 synchronously displays, among images included in a plurality of video files corresponding to timelines displayed in the timeline display area DA3, a plurality of images associated with a time code of a certain time point included in the timelines displayed in the timeline display area DA3.

For example, if an icon on a left side of a divided aspect selection portion 1425 (see FIG. 12) is selected by a user operation input, the synchronous display area DA1 displays a video file inputted from the camera 111 on the main screen and displays a video file inputted from the cameras 112 to 114 on the sub-screens (see FIG. 5).

If an icon on a right side of the divided aspect selection portion 1425 is selected by a user operation input, the synchronous display area DA1 displays four video files inputted from the cameras 111 to 114 in equally divided four display areas (see FIG. 6).

When it is attempted to synchronously reproduce a plurality of video files in the synchronous display area DA1, reading time difference occurs in starting or reproducing the video files due to difference among bit rates of the video files. The magnitude of the reading time difference is not constant because it is influenced by processing capacities of the server apparatus 130, the viewing terminal apparatus 140 and a network line (not shown in the drawings) connecting these. Therefore, communication about buffer time is performed among functions of reproducing video files on each screen (hereinafter referred to as reproduction players) in the viewing terminal apparatus 140 to solve the above problem.

For example, in the case of reproducing a video file on one screen (for example, the main screen), all data of the video file is not read at the first stage, but, for example, data corresponding to the first five seconds is read, and, while the data is being reproduced, data corresponding to the next five seconds is read. By sequentially repeating this, continuous reproduction is realized.

By utilizing time required to cause such data corresponding to a predetermined time to be stored into a buffer, a configuration is made in which, for example, in the case of simultaneously starting reproduction on one screen (for example, the main screen) and another screen (for example, a sub-screen), when the reproduction player of the main screen has finished reading of data of a video file corresponding to five seconds, the reproduction player of the main screen notifies the reproduction player of the sub-screen to that effect and reproduction of the both reproduction players are started being triggered by the notification.

Note that such notification is not limited to the case where reproduction is simultaneously started on a plurality of reproduction players but may be further performed in a case where, while a video file is being reproduced on one reproduction player, reproduction of a video file started on another reproduction player, case where, while video files are being reproduced on a plurality of reproduction players, reproduction of video files are discontinued (a time zone during which recording is not performed starts) on a part of the reproduction players, and the like.

On the related information display area DA2, information related to video files being displayed in the synchronous display area DA1 is acquired from the server apparatus 130 or an external apparatus (or system) not shown in the drawings and selectively displayed.

For example, when an "Event" tag is selected in the related information display area DA2 (in a state shown in FIG. 5 and the like), event information about a surgical operation (about start of the operation, start of anesthetic administration and the like) and time information corresponding to the event information, which have been inputted from an external system that manages anesthetic administration is displayed in the related information display area DA2, the external system not being shown in the drawings.

When a "Comment" tag is selected in the related information display area DA2 (a state shown in FIG. 8), times (time codes) corresponding to still images captured by capture processing to be described later and comments attached to the still images by the user are displayed in the related information display area DA2.

When a "Section" tag is selected in the related information display area DA2 (a state shown in FIG. 14), a time zone specified by section identification processing to be described later are displayed in the related information display area DA2. In description below, the section means a time zone specified by the section identification processing.

When a "Surgical Procedure" tag is selected in the related information display area DA2 (not shown in the drawings), video files and information related to the video files, which are recorded in the server apparatus 130, are displayed in the related information display area DA2 based on the same surgical procedure as video files being synchronously displayed in the synchronous display area DA1.

When a "Diagnosed Name" tag is selected in the related information display area DA2 (not shown in the drawings), video files and information related to the video files, which are recorded in the server apparatus 130, are displayed in the related information display area DA2 based on the same diagnosed name as video files being reproduced in the synchronous display area DA1.

When a "Video File of Same Patient" tag is selected in the related information display area DA2 (not shown in the drawings), video files and information related to the video files, which are recorded in the server apparatus 130, being associated with the same patient ID as video files being reproduced in the synchronous display area DA1, are displayed in the related information display area DA2.

Note that the pieces of information displayed in the related information display area DA2, which have been enumerated here, are mere examples, and information other than the pieces of information enumerated here may be displayed in the related information display area DA2, or at least a part of the pieces of information enumerated here may not be displayed. Further, as for the layout at the time of displaying various kinds of information in the related information display area DA2, layouts shown in the drawings are only examples, and the layout of the related information display area DA2 is not restricted to what have been shown in the drawings at the time of practicing the present invention.

The event, information and time information inputted from the external system not shown in the drawings are inputted to the server apparatus 130, associated with video files about the surgical operation and accumulated in the server apparatus 130 together with the video files. In other words, an external input unit of the present invention is configured with the server apparatus 130.

As is apparent from comparison between FIGS. 5 and 6, rates of the synchronous display area DA1 and the related information display area DA2 occupying the display area of the viewing terminal apparatus 140 are different between the case of divided displays on the main screen and the sub-screens and the case of even division into four. The synchronous display area DA1 and the related information display area DA2 in the latter case are smaller and larger, respectively, in comparison with the former case.

The timeline display area DA3 displays timelines indicating time zones corresponding to a plurality of video files about a surgical operation for the input systems (the cameras 111 to 114), respectively.

Here, the timeline is a linear or belt-shaped display and indicates in which time zone a video file is recorded or in which time zone the video file is not recorded.

It is preferable that the timelines displayed in the timeline display area DA3 are displayed based on a time code associated with video files related to the timelines. Further, it is preferable that the timelines are identifiably in different display aspects (for example, the timelines are in different colors).

In the timeline display area DA3, besides the timelines, a cursor 1414 showing a time point of being synchronously displayed in the synchronous display area DA1 is displayed, being superimposed on the timelines (see FIG. 10).

The cursor 1414 in the present embodiment is configured with a window frame in which the time point (both of the time and elapsed time from recording start time) is displayed, and a linear display extending over the plurality of input systems.

The cursor 1414 is provided not only with the role of showing a time point of being synchronously displayed in the synchronous display area DA1 but also with, for example, a function of, by being slid left or right along a time axis by a user operation, causing video files at a time point freely specified by the user to be synchronously displayed in the synchronous display area DA1.

Above and below a timeline displayed in the timeline display area DA3, tag displays are displayed.

Here, a tag display displayed above the timeline shows time (a time code) associated with event information displayed when the "Event" tag in the related information display area DA2 is selected, on the timeline. For example, a tag display 1413 in FIG. 10 is a tag display attached above a timeline about the camera 111 (a timeline shown as "Video. 1") and is associated with event information 1412 of "16:50:15 Start Operation" shown in FIG. 7.

A tag display displayed below the timeline shows time (a time code) associated with comment information displayed when the "Comment" tag in the related information display area DA2 is selected. For example, a tag display 1415 in FIG. 10 is a tag display attached below the timeline about the camera 111 and is associated with comment information 1407 of "17:04:08 Conference 1" shown in FIG. 8 (which is inputted by comment processing to be described later) and a still image 1404 at the same time (captured by the capture processing to be described later).

In order to attach the tag displays described above to the timeline, the server apparatus 130 executes first tag processing and second tag processing as shown below.

The first tag processing is processing for, in association with a time code of a certain time point included in a timeline displayed in the timeline display area DA3, attaching a tag display below the timeline.

The second tag processing is processing for, in association with the time code of the certain time point included in the timeline displayed in the timeline display area DA3, attaching a tag display above the timeline, based on event information and time information inputted from the external system.

While the first tag processing is processing performed, being triggered by a user operation input to the viewing terminal apparatus 140 (specifically an operation of a capture icon 1426 to be described later), the second tag processing is different in that it is processing automatically performed, being triggered by predetermined information being inputted from an external system.

For either of the tag displays attached to above and below the timeline, by specifying the tag display with the pointer 1401, time points synchronously displayed in the synchronous display area DA1 can be changed to time (a time code) associated with the specified tag display. At this time, a display position of the cursor 1414 also moves to a position corresponding to the time.

For either of the tag displays attached above and below the timeline, if time (a time code) shown by the tag display corresponds to a time point shown by the cursor 1414 (time points synchronously displayed in the synchronous display area DA1), event information or comment information associated with the time is superimposedly displayed in a display area of a video file of an input system corresponding to the timeline to which the tag display is attached.

In the case of divided displays on the main screen and the sub-screens, when the pointer 1401 is superimposed on the main screen, a full-screen display icon 1402 is displayed on the center of the main screen, an input system display 1403 showing an input system corresponding to a video file being reproduced on the main screen is displayed on an upper right corner part of the main screen, and still images captured from the video file being reproduced on the main screen (what are captured by the capture processing to be described later) are shown on a lower part of the main screen (see FIG. 7).

At this time, by operating the full-screen display icon 1402 with the pointer 1401, the video file being reproduced on the main screen is full-screen displayed (not shown in the drawings).

In the above case, if the pointer 1401 is superimposed on a still image displayed on the lower part of the main screen (for example, the still image 1404), a comment editing icon 1405 and a deletion icon 1406 are displayed in the display area of the still image 1404. Then, comment information 1403 similar to the comment information 1407 associated with the still image 1404 is displayed on the main screen (see FIG. 8).

When the deletion icon 1406 is operated with the pointer 1401, the target still image 1404 and the comment information 1407 associated therewith are deleted and disappear from the display area of the viewing terminal apparatus 140.

Since processing about the comment editing icon 1405 corresponds to the editing processing of the present invention, the processing will be described later.

In the case of divided displays on the main screen and the sub-screens, when the pointer 1401 is superimposed on a sub-screen, a full-screen display icon 1409 and a display switching icon 1410 are displayed on the sub-screen, and an input system display 1411 showing an input system corresponding to a video file being reproduced on the sub-screen is displayed on an upper right corner portion of the sub-screen (see FIG. 9).

At this time, by operating the full-screen display icon 1409 with the pointer 1401, the video file being reproduced on the sub-screen is full-screen displayed (not shown in the drawings).

Further, at this time, by operating the display switching icon 1410 with the pointer 1401, the video file being reproduced on the sub-screen is exchanged for a video file being reproduced on the main screen (not shown in the drawings).

On a lower left part of the timeline display area DA3, reproduction speed selection icons 1416 are disposed (see FIG. 10).

The reproduction speed selection icons 1416 are icons for selecting a reproduction speed of video files being synchronously displayed in the synchronous display area DA1.

More specifically, the reproduction speed selection icons 1416 are operation icons for selecting "0.5× speed", "1× speed", "1.5× speed", "2× speed", "4× speed", "6× speed" and "8× speed" shown in FIG. 10 in that order from a left side.

Note that the reproduction speed alternatives enumerated here are only an example, and can be appropriately changed in practicing the present invention.

On a lower center part of the timeline display area DA3, operation icons for reproduction control are disposed (see FIG. 11).

A forward jump icon 1417 is an operation icon for causing a display position of the cursor 1414 (a time point of being synchronously displayed in the synchronous display area DA1) to jump to a display position of the nearest "Comment" tag on a forward side of the display position.

A 30-second backward icon 1418 is an operation icon for changing a time point of being synchronously displayed in the synchronous display area DA1 to a time point thirty seconds before.

A 10-second backward icon 1419 is an operation icon for changing a time point of being synchronously displayed in the synchronous display area DA1 to a time point ten seconds before.

A reproduction icon 1420 is an operation icon for causing reproduction of video files to start in the synchronous display area DA1.

A stop icon 1421 is an operation icon for causing reproduction of video files in the synchronous display area DA1 to stop.

A 10-second forward icon 1422 is an operation icon for changing a time point of being synchronously displayed in the synchronous display area DA1 to a time point ten seconds after.

A 30-second forward icon 1423 is an operation icon for changing a time point of being synchronously displayed in the synchronous display area DA1 to a time point thirty seconds after.

A backward jump icon 1424 is an operation icon for causing a display position of the cursor 1414 (a time point of being synchronously displayed in the synchronous display area DA1) to jump to a display position of the nearest "Comment" tag on a backward side of the display position.

Note that the operation icons for reproduction control enumerated here are only examples. An operation icon for reproduction control other than the operation icons enumerated here may be provided, or at least a part of the operation icons for reproduction control enumerated here may be omitted.

Further, the functions of the operation icons for reproduction control enumerated here are mere examples. In practicing the present invention, operation icons provided in similar display aspects may realize different functions. For example, the forward jump icon 1417 or the backward jump icon 1424 may be such that causes a display position of the cursor 1414 to jump to a display position of the nearest "Event" tag on a forward side or a backward side of the display position.

On a lower right part of the timeline display area DA3, operation icons as below are disposed (see FIG. 12).

When an icon on a left side of a divided aspect selection portion 1425 is operated, the synchronous display area DA1 is divided into the main screen and the sub-screens (see FIG. 5). When an icon on a right side is operated, the synchronous display area DA1 is divided into four (see FIG. 6).

Time axis selection icons 1428 are buttons to accept an operation of increasing/decreasing a display width of a unit time (one minute in the present embodiment) of a time axis (a horizontal axis) in the timeline display area DA3. More specifically, the time axis selection icons 1428 are an operation icon to maximize the display width of the unit time of the time axis in the timeline display area DA3, an operation icon to cause the display width to be wider by one stage, an operation icon to cause the display width to be narrower by one stage and an operation icon to minimize the display width, in that order from a left side in FIG. 12.

The capture icon 1426 is an operating icon for capturing a still image from video files being synchronously displayed in the synchronous display area DA1.

Since each processing about the capture icon 1426 corresponds to the editing processing of the present invention, the processing will be described later.

<Editing Processing of Video Files Synchronously Displayed>

Next, editing processing of video files synchronously displayed in the synchronous display area DA1 will be described with reference to FIGS. 13 to 15.

Figure 13:
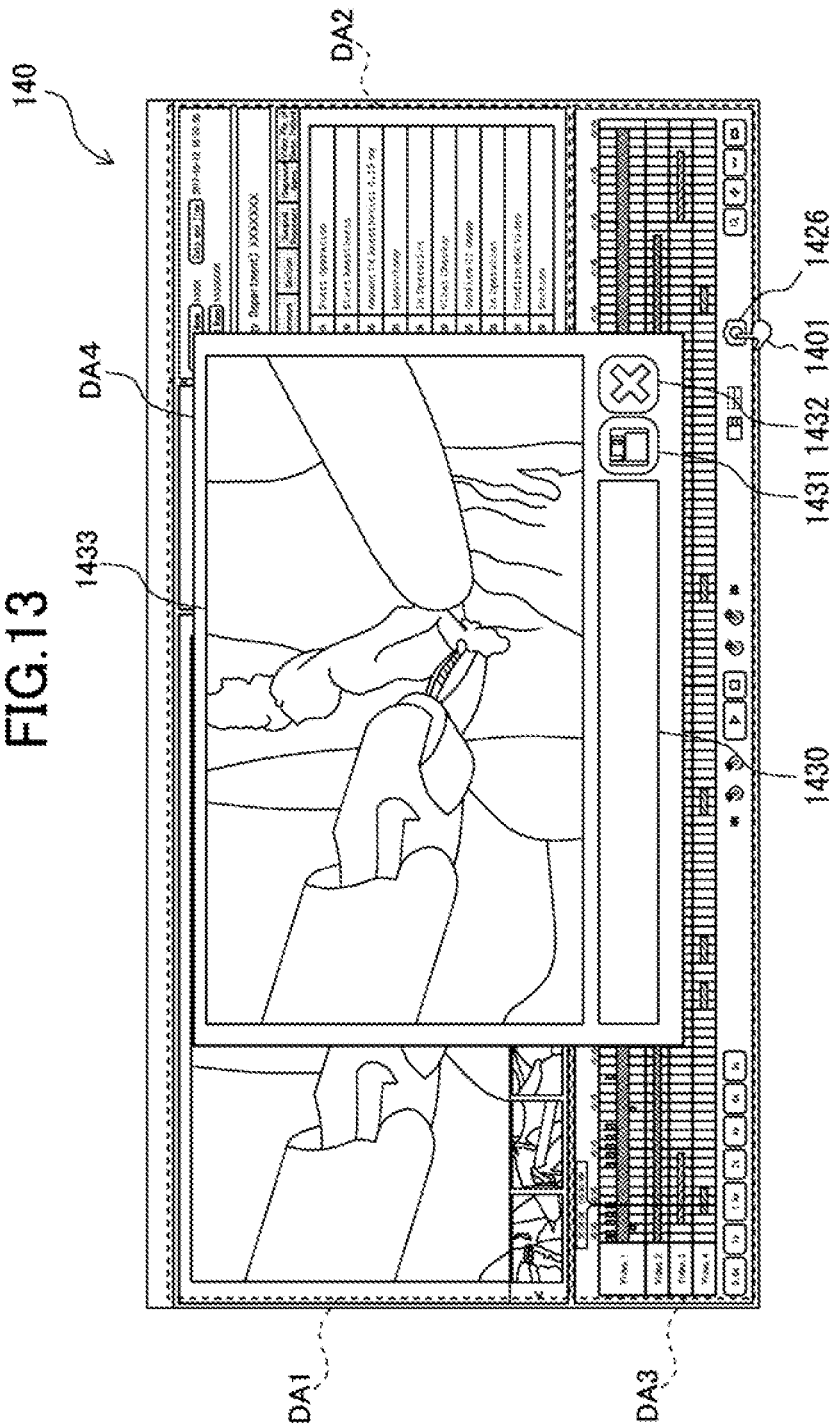
FIG. 13 is a diagram showing a specific example of a case where a capture processing screen is popped up on the viewing terminal apparatus.

FIG. 13 is a diagram showing a specific example in a case where a capture processing screen DA4 is popped up on the viewing terminal apparatus 140. FIG. 14 is a diagram showing a specific example in a case where the "Section" tag is selected on the viewing terminal apparatus 140. FIG. 15 is an enlarged view in which the related information display area DA2 in the case where the "Section" tag is selected is enlarged.

When the capture icon 1426 is operated with the pointer 1401, the capture processing screen DA4 for accepting an operation about the capture processing is popped up on the viewing terminal apparatus 140 (see FIG. 13).

Here, to be "popped up" refers to being displayed on a front (a higher layer) of other display areas (for example, the synchronous display area DA1, the timeline display area DA3 and the like) displayed on the viewing terminal apparatus 140.

In the capture processing screen DA4, an image of a video file synchronously displayed in the synchronous display area DA1 at a time point of operating the capture icon 1426 (in FIG. 13, an image of the main screen (an image of Video. 1)) is captured and displayed as a still image 1433.

In the capture processing screen DA4, a comment input field 1430 for inputting comment information, a storage icon 1431 for storing a captured still image and a deletion icon 1432 for erasing display on the capture processing screen DA4 (stopping the capture processing) are also displayed in addition to the still image 1433.

In the comment input field 1430, the user can input a given comment information based on a user operation input to an operation unit not shown in the drawings (for example, a keyboard or the like).

When the storage icon 1431 is operated with the pointer 1401 after text information is inputted to the comment input field 1430, the inputted comment information is stored into the server apparatus 130, being associated with the still image 1433 and a time code corresponding to the still image 1433.

When the storage icon 1431 is operated with the pointer 1401 without inputting text information to the comment input field 1430, comment information from which it can be recognized that text information has not been inputted (for example, "Untitled" or the like) is stored into the server apparatus 130, being associated with the still image 1433 and the time code corresponding to the still image 1433.

The capture processing screen DA4 is similarly popped up on the viewing terminal apparatus 140 when the comment editing icon 1405 is operated, without being limited to the case where the capture icon 1426 is operated.

A display aspect of the capture processing screen DA4 and processing performed according to an operation of each operation icon are similar to the above description, detailed description thereof will not be repeated.

The following is a summary of the capture processing described above.

First, the server apparatus 130 can execute the capture processing for capturing an image included in a video file corresponding to a timeline displayed in the timeline display area DA3 as a still image according to an operation of the capture icon 1426.

Furthermore, when the above capture processing is executed, the server apparatus 130 can execute the first tag processing for attaching a tag display below the timeline in association with a time code (that is, a time code of a certain time point included in the time line) corresponding to the image and comment processing for inputting a given comment in association with the time code corresponding to the tag display attached by the first tag processing, based on a user operation input together.

In other words, the operation of the capture icon 1426 is a user operation input to be a trigger for the capture processing, the first tag processing and the comment processing. Note that it is shown in each diagram of the present embodiment as if the timeline targeted by the above capture processing and first tag processing were only the timeline of "Video. 1" (the timeline about the camera 111), similar processing may be executed for the other timelines (timelines about the cameras 112 to 114) as a target.

At the time of executing the capture processing as described above, the user using the medical video processing system 100 can execute the capture processing, referring to video files displayed in the synchronous display area DA1, related information displayed in the related information display area DA2, and timelines (time-series information) displayed in the timeline display area DA3. Therefore, the user can easily find a desired still image from the video files displayed in the synchronous display area DA1 and store the still image.

Figure 14:
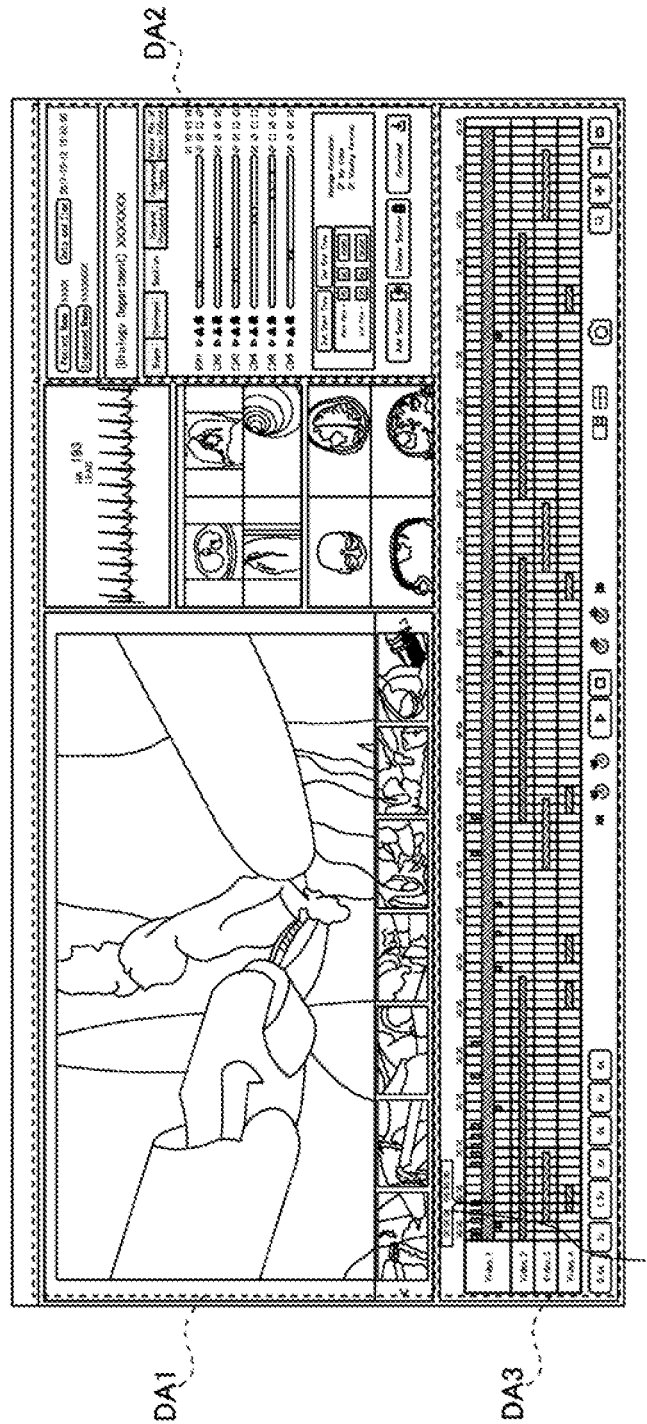
FIG. 14 is a diagram showing a specific example of a case where a "Section" tag is selected on the viewing terminal apparatus.

Next, when the "Section" tag in the related information display area DA2 is operated with the pointer 1401, various operation icons and the like for accepting an operation about the section identification processing and a list of sections specified by the section identification processing are displayed (see FIG. 14).

Note that, although description will be made on an embodied aspect in which the operation icons and the like about the section identification processing are displayed in the related information display area DA2 in the present embodiment, another display area including the operation icons about the section identification processing may be popped up on the screen of the viewing terminal apparatus 140 similarly to the capture processing.

Figure 15:
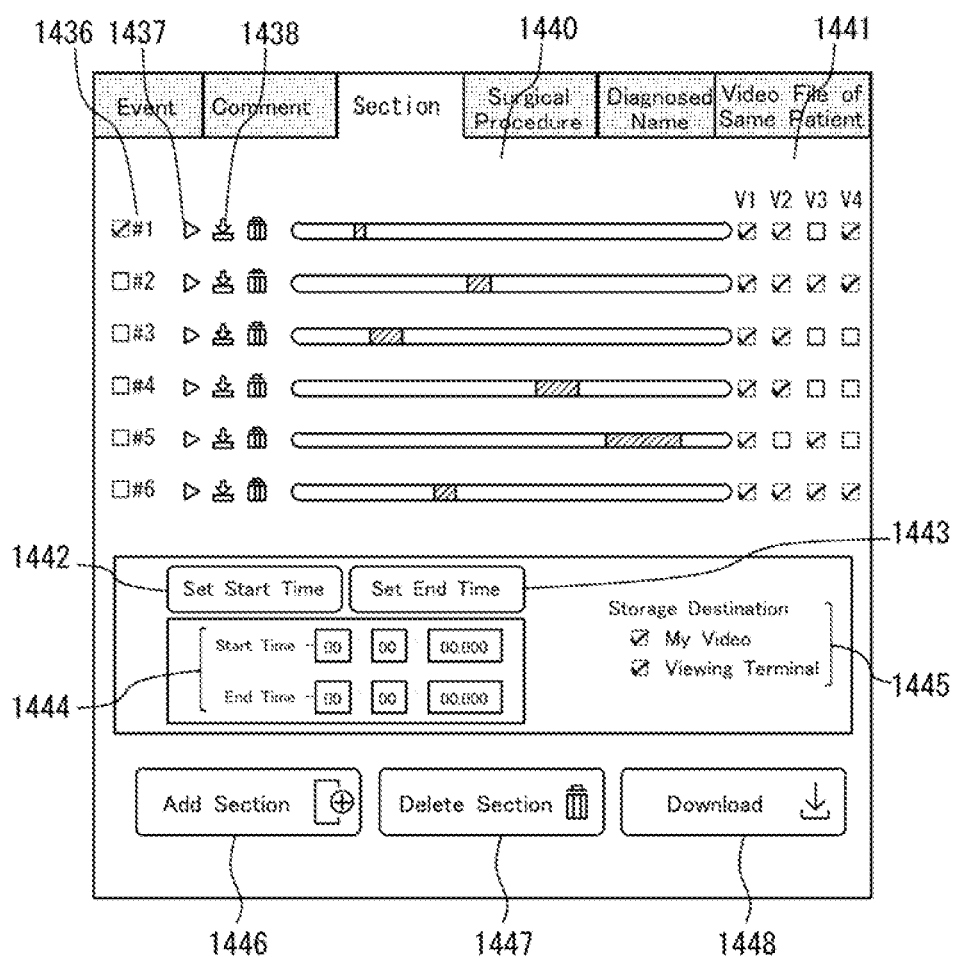
FIG. 15 is an enlarged view in which a related information display area in the case where the "Section" tag is selected is enlarged.

The following are displayed in the "Section" tag in the related information display area DA2 (see FIG. 15).

A section display portion 1440 displays sections specified before. In the case of an example shown in FIG. 15, in the section display portion 1440, the whole time zone in which recording is performed is indicated by a solid-color timeline, and which time zone in the whole time zone each section specified by the section identification processing corresponds to is indicated by a shaded area. Here, "the whole time zone in which recording is performed" refers to a total of time zones in which at least one of the cameras 111 to 114 performs shooting in the period during which the surgical operation is performed. In the present embodiment, since a video file inputted from the camera 111 is such that is recorded through a period during which a surgical operation is performed, a time zone indicated by a timeline corresponding to the video file (the timeline shown as "Video. 1" in FIG. 5 and the like) is equal to "the whole time zone". In other words, the solid-color part of each timeline in the section display portion 1440 indicates a time length equal to recording time of the video file of "Video. 1" displayed in the synchronous display area DA1.

Input system specification boxes 1441 are checkboxes to specify, for each section (a time zone indicated by a shaded part) displayed in the section display portion 1440, input systems (among the cameras 111 to 114) targeting the sections. For example, if checkboxes indicated by "V1", "V2", "V3" and "V4" are checked, video files inputted from the camera 111, the camera 112, the camera 113 and the camera 114, respectively, are targeted. The user can optionally check or uncheck each checkbox by an operation with the pointer 1401. However, a configuration is made in which, if a video file of an input system corresponding to a checkbox does not exist in each section (if recording is not performed), checking of the checkbox is disabled, so that useless specification cannot be performed.

A section number display portion 1436 includes identification numbers of the sections (for example, what are indicated by "#1" to "#6", or the like) and checkboxes specifying the sections. The checkboxes included in the section number display portion 1436 are used for processing corresponding to an operation of a section deletion icon 1447 or a download icon 1448 to be described later.

Each of individual reproduction icons 1437 is an operation icon to accept an operation of causing video files associated with a corresponding section to be synchronously displayed in the synchronous display area DA1. Video files synchronously displayed according to an operation of each of the individual reproduction icons 1437 correspond to a section displayed in the section display portion 1440 and are video files of input systems specified by the input system specification boxes 1441.

Each of individual download icons 1438 is an operation icon to accept an operation of causing a corresponding section to be downloaded to a specified storage destination (a storage area specified by any of storage destination checkboxes 1445 to be described later). Video files downloaded according to an operation of each of the individual download icons 1433 correspond to a section displayed in the section display portion 1440 and are video files of input systems specified by the input, system specification boxes 1441.

A start/end input field 1444 is a display field to accept an input of a start time point and an end time point specified by the section identification processing. The start/end input field 1444 is configured with a field to input a numerical value in "hours", a field to input a numerical value in "minutes" and a field to input a numerical value in "seconds" in that order from a left side. In each field of the start/end input field 1444, the user can input a given numerical value based on a user operation input to the operation unit not shown in the drawings (for example, the keyboard or the like).

A start time point setting icon 1442 is an operation icon to accept an operation of inputting a display position of the cursor 1414 (a time point of being displayed in the synchronous display area DA1) to a start time point display field in the start/end input field 1444.

An end time point setting icon 1443 is an operation icon to accept an operation of inputting a display position of the cursor 1414 (a time point of being synchronously displayed in the synchronous display area DA1) to an end time point display field in the start/end input field 1444.

The storage destination checkboxes 1445 are checkboxes to specify a storage area to be a storage destination in download processing performed according to an operation of any of individual download icons 1438 or the download icon 1448. In FIG. 15, a storage area indicated by "My Video" means a storage area provided in the server apparatus 130 for a user who is logged in at that time, and "Viewing Terminal" means a storage area provided in the viewing terminal apparatus 140 that the user is viewing at that time point.

A section addition icon 1446 is an operation icon to accept an operation of adding a section to be displayed in the section display portion 1440, according to a start time point and an end time point inputted in the start/end input field 1444 at that time point.

The section deletion icon 1447 is an operation icon to accept an operation of deleting a section corresponding to a checkbox in the section number display portion 1436 that is checked at that time point (erasing the section from a list displayed in the section display portion 1440).

The download icon 1448 is an operation icon to accept an operation of causing a video file of an input system which corresponds to a section for which a corresponding checkbox in the section number display portion 1436 is checked at that time point and is specified by an input system specification box 1441 for each section to be downloaded to a storage area specified by any of the storage destination checkbox 1445.

The server apparatus 130 executes the section identification processing for identifying a time zone from a time code of a start time point (a first time point) to a time code of an end time point (a second time point) that are included in a time line displayed in the timeline display area DA3, based on such inputs and settings as described above.

The server apparatus 130 can execute download processing for, from a video file associated with the time codes included in the time zone (a section) identified by the section identification processing, downloading a video part of the time zone. In a case where a plurality of video files associated with time codes included in the section are specified like the section indicated by "#1", the server apparatus 130 can execute the download processing for the specified plurality of video files in batch.

Since such download processing as described above can be executed, a user using the medical video processing system 100 can easily obtain one or more new video files in which only a video part shot during a desired time zone is extracted.

<About Modification of the Present Invention>

Although the present invention has been described so far based on the embodiment described with reference to each drawing, the present invention is not limited to the above embodiment but includes various aspects such as modifications, improvements and the like as far as the object of the present invention is achieved.

Although the description has been made on the assumption of the components shown in FIG. 1 in the above description of the embodiment, each component of the present invention is only required to be formed to realize its functions. Therefore, each component of the present invention is not required to be an individual independent existence. It is permitted for a plurality of components to be formed as one member, for one component to be formed by a plurality of members, for a certain component to be a part of another component, for a part of a certain component and a part of another component are overlapped, and the like.

For example, in the medical video processing system according to the present invention, shooting apparatuses corresponding to the cameras 111 to 114 may not be included; processing may be performed for a video file inputted from a shooting apparatus outside the system; and processing may be performed for a video file inputted from an apparatus different, from a shooting apparatus (for example, a medical measurement apparatus or the like).

The various operations stated in the above embodiment are mere specific examples, and practicing of the present invention is not limited thereto. Therefore, each of the above operations may be replaced with a different operation; a part of the operations may be omitted; and another operation that is not described in the embodiment may be added.

The various display aspects stated in the above embodiment are mere specific examples, and practicing of the present invention is not limited thereto. Therefore, each of the above displays may be replaced with a different display; a part of the displays may be omitted; and another display that is not described in the embodiment may be added.

The various kinds of editing processing stated in the above embodiment are mere specific examples, and practicing of the present invention is not limited thereto. Therefore, a part of each editing processing described above may be omitted, and another editing processing that is not described in the embodiment may be added.

For example, although it is shown as if a timeline to which a tag display were attached by the above first tag processing and second tag processing were only the timeline corresponding to the camera 111, a tag display may be attached to another time line.

In the embodiment stated above, description has been made on the assumption that a video file inputted from the camera 111 is recorded through a period during which a surgical operation is performed, and a timeline about the video file (the timeline shown as "Video. 1" in FIG. 5 and the like) is equal to what indicates the period during which the surgical operation is performed. Practicing of the present invention, however, is not limited to this aspect. In other words, in practicing of the present invention, it is not necessarily required that a video file recorded through a period during which a surgical operation is performed exists, and all video files synchronously displayed in the viewing terminal apparatus 140 (the synchronous display area DA1) may be such that include a time zone in which recording is stopped.

In the above embodiment, a method for identifying a section targeted by the download processing, using an operation icon or the like displayed in the "section" tag in the related information display area DA2 has been described. However, processing for identifying a section is not limited to such a method, but input by a method below is also possible.

For example, it is also permitted that a tag display above or below a time line (a tag display attached by the first tab processing or the second tag processing) is specified with the pointer 1401, and time (a time code) associated with the specified tag display is inputted as a start time point or an end time point of a section. In other words, at least in a part in the case of executing the section identification processing, at least one of the section start time point (the first time point) and the section end time point (the second time point) may be identified based on a user operation input specifying a tag display attached by the first tag processing or the second tag processing.

The display position of each operation icon stated in the above embodiment is a mere example, and practicing of the present invention is not limited thereto. For the operation icons related to the editing processing of the present invention, however, it is preferable that the operation icons are displayed at such positions that it is possible to operate the operation icons while referring to the timeline display area and the synchronous display area. In other words, it is preferable that the operation icons related to the editing processing of the present invention are displayed on a display unit where the timeline display area and synchronous display area of the present invention are displayed. Here, the concept of being "displayed on a display unit where the timeline display area and synchronous display area are displayed" is not limited to being displayed in the same display frame (window) but includes being displayed in separate display frames like the above embodiment (see FIGS. 13 and 14), being separately displayed on a plurality of display apparatuses (a multi-monitor) under the control of the same platform, and the like.

The present embodiment includes the following technical thoughts:

(1) A medical video processing system including: a video input unit that inputs a plurality of video files about a surgical operation, separating the plurality of video files according to a plurality of input systems;

a storage unit that stores the plurality of video files inputted by the video input unit in association with a common time code specified with a certain time point in a period during which the surgical operation is performed as a start point;

a display unit that displays the plurality of video files stored in the storage unit and information about the video files; and an operation input unit that accepts an operation input by a user to the display unit; wherein a display area of the display unit includes:

a timeline display area to display a plurality of timelines indicating time zones corresponding to the plurality of video files about the surgical operation, separating the plurality of timelines according to the input systems; and a synchronous display area to synchronously display, among images included in the plurality of video files corresponding to the timelines displayed in the timeline display area, at least a part of a plurality of images associated with the time code of the certain time point included in the time lines; and the medical video processing system further includes an editing unit that executes editing processing about the video files synchronously displayed in the synchronous display area, based on an operation input accepted by the operation input unit.

(2) The medical video processing system according to (1), wherein the editing unit executes:

first tag processing for, in association with the time code of the certain time point included in the time lines displayed in the timeline display area, attaching a tag display to the time lines, based on an operation input by the user; and comment processing for inputting a given comment in association with the time code corresponding to the tag display attached by the first tag processing, based on an operation input by the user.

(3) The medical video processing system according to (2), wherein in the case of executing capture processing for capturing an image included in the video files corresponding to the timelines displayed in the timeline display area as a still image, the editing unit executes the first tag processing to attach a tag display in association with a time code corresponding to the image.

(4) The medical video processing system according to (2) or (3), wherein the editing unit executes:

identification processing for identifying a time zone from a time code of a first time point to a time code of a second time point included in the time lines displayed in the timeline display area, based on an operation input by the user; and download processing for, from a video file associated with a time code included in the time zone identified by the identification processing, downloading a video part of the time zone.

(5) The medical video processing system according to (4), wherein when a plurality of video files associated with the time codes included in the time zone identified by the identification processing are specified, the editing unit executes the download processing for the plurality of video files.

(6) The medical video processing system according to (4) or (5), wherein at least in a part in the case of executing the identification processing, at least one of the first time point and the second time point is identified based on an operation input by the user specifying the tag display attached by the first tag processing.

(7) The medical video processing system according to any one of (1) to (6), including:

an external input unit that inputs event information about the surgical operation and time information corresponding to the event information from an external system; wherein the editing unit executes second tag processing for, in association with the time code of the certain time point included in the time lines displayed in the timeline display area, attaching a tag display to the time lines, based on the event information and the time information inputted by the external input unit.

(8) The medical video processing system according to (7) depending on (4) to (6), wherein at least in a part in the case of executing the identification processing, at least one of the first time point and the second time point is identified based on an operation input by the user specifying the tag display attached by the second tag processing.

(9) The medical video processing system according to any one of (1) to (8), including:

a plurality of shooting apparatuses that shoot a surgical field of the surgical operation and a biological information monitor displaying biological information about a surgically operated person of the surgical operation; and a shooting control unit that performs control about shooting by the plurality of shooting apparatuses, based on an operation by the user; wherein a plurality of video input units input video files for the plurality of shooting apparatuses, respectively, each of the plurality of video input units being the input video unit.

The present application claims priority based on Japanese Patent Application No. 2017-251482 filed to Japan on Dec. 27, 2017, all the disclosure of which is incorporated herein.

REFERENCE SIGNS LIST

100: medical video processing system
111, 112, 113, 114: camera
120: encoder
130: server apparatus
140: viewing terminal apparatus
1201: input screen
1202: output screen
1203: state display
1204: recording start button
1205: recording stop button
1206: still image shooting button
1207: recording pause button
1208: surgical operation information display
1209: output information display
1210: extended display activation button
1211, 1212, 1213: sub-screen
1214: extended display stop button
1401: pointer
1402, 1409: full-screen display icon
1403: input system display
1404: still image
1405: comment editing icon
1406: deletion icon
1407, 1408: comment information
1410: display switching icon
1411: input system display
1412: event information
1413, 1415: tag display
1414: cursor
1416: reproduction speed selection icon
1417: forward jump icon
1418: 30-second backward icon
1419: 10-second backward icon
1420: reproduction icon
1421: stop icon
1422: 10-second forward icon
1423: 30-second forward icon
1424: backward jump icon
1425: divided aspect selection portion
1426: capture icon
1428: time axis selection icon
1430: comment input field
1431: storage icon
1432: deletion icon
1433: still image
1436: section number display portion
1437: individual reproduction icon
1438: individual download icon
1440: section display portion
1441: input system specification box
1442: start time point setting icon
1443: end time point setting icon
1444: start/end input field
1445: storage destination checkbox
1446: section addition icon
1447: section deletion icon
1448: download icon
DA1: synchronous display area
DA2: related information display area
DA3: timeline display area
DA4: capture processing screen

The invention claimed is:

1. A medical video processing system comprising:

a video input unit that inputs a plurality of video files about a surgical operation, said plurality of video files recording the surgical operation for a whole time zone, the plurality of video files comprising:

a first video file comprising first frames of images taken by a first input system to take the surgical operation for a first timeline in the whole time zone, and a second video file comprising second frames of images taken by a second input system to take the surgical operation for a second timeline in the whole time zone, each of the first frames having a time code that is common to that of each of the second frames, the time code specifying when each of the images is taken;

a storage unit that stores the plurality of video files;

a display unit that displays the plurality of video files stored in the storage unit, the display unit comprising a timeline display area and a synchronous display area; and an operation input unit that accepts an operation input by a user to the display unit;

wherein the timeline display area displays the first timeline and the second timeline, wherein the synchronous display area synchronously displays each of the images of the first frames and each of the second frames, wherein said each of the images of the first frames and said each of the images of the second frames synchronously displayed with said each of the images of the first frames have the same time code; and wherein the medical video processing system further comprises an editing unit that executes download processing based on the operation input at the operation input unit, wherein the editing unit executes:

a first processing step for identifying a section or sections of the whole time zone based on the operation input at the operation input unit; and a second processing step for identifying the section or sections to be downloaded among the section or sections identified in the first processing step, based on the operation input at the operation input unit; and a third processing step for identifying the video files to be download among said plurality of the video files based on the operation input at the operation input unit, wherein, when the editing unit that executes the download processing, the video files identified in the third processing step are edited in batch, thereby downloading a plurality of video file parts edited from the video files identified in the third processing step, each video file part of the video file parts synchronously corresponding to the section identified by the second processing step.

2. The medical video processing system according to claim 1, wherein the editing unit executes:

first tag processing for attaching a tag display to the time code of the first timeline displayed in the timeline display area based on an operation input by the user; and comment processing for inputting a given comment in association with the time code corresponding to the tag display based on an operation input by the user.

3. The medical video processing system according to claim 2, wherein, in the case of executing capture processing for capturing each of the images included in the first video file having the first timeline or the second video file having the second timeline displayed in the timeline display area as a still image, the editing unit executes the first tag processing to attach the tag display in association with the time code corresponding to the still image.

4. The medical video processing system according to claim 2, wherein at least in a part in the case of executing the identification processing, at least one of a first time point and a second time point is identified based on the operation input by the user specifying the tag display attached by the first tag processing.

5. The medical video processing system according to claim 2, comprising an external input unit that inputs event information about the surgical operation and time information corresponding to the event information from an external system; wherein the editing unit executes second tag processing for, in association with the time code of the certain time point included in the first timeline displayed in the timeline display area, attaching the tag display to the first timeline, based on the event information and the time information inputted by the external input unit.

6. The medical video processing system according to claim 5, wherein at least in a part in the case of executing the identification processing, at least one of a first time point and a second time point is identified based on the operation input by the user specifying the tag display attached by the second tag processing.

7. The medical video processing system according to claim 1, comprising:

a plurality of shooting apparatuses comprising a first shooting apparatus and a second shooting apparatus, wherein each of the first shooting apparatus and the second shooting apparatus shoots a surgical field of the surgical operation and a biological information monitor displaying biological information about a surgically operated person of the surgical operation; and a shooting control unit that performs control about shooting by the plurality of shooting apparatuses, based on an operation by the user; wherein the first shooting apparatus is provided for the first input system to take the first frames of the images, the second shooting apparatus is provided for the second input system to take the second frames of the images.

* * * * *